United States Patent [19]

Haining

[11] Patent Number: 5,714,429
[45] Date of Patent: Feb. 3, 1998

[54] SUPPORTED HETEROPOLYACID CATALYST ON A SILICA SUPPORT FORMED BY FLAME HYDROLYSIS

[75] Inventor: Gordon John Haining, Falkirk, Scotland

[73] Assignee: BP Chemicals Limited, London, England

[21] Appl. No.: 461,435

[22] Filed: Jun. 5, 1995

[30] Foreign Application Priority Data

Sep. 26, 1994 [GB] United Kingdom ............ 9419387

[51] Int. Cl.$^6$ .................................................. B01J 21/08
[52] U.S. Cl. .................... 502/232; 502/407; 502/408; 502/240; 502/224; 502/208; 502/210; 502/211
[58] Field of Search ............................. 502/407, 408, 502/232, 240, 224, 208, 210, 211

[56] References Cited

U.S. PATENT DOCUMENTS

| | | | |
|---|---|---|---|
| 2,173,187 | 9/1939 | Tanner | 260/641 |
| 3,231,518 | 1/1966 | Church | 502/232 |
| 3,996,338 | 12/1976 | Frampton | 423/335 |
| 4,012,452 | 3/1977 | Frampton | 260/641 |
| 4,038,211 | 7/1977 | Frampton | 252/435 |
| 4,808,559 | 2/1989 | Sommer et al. | 502/63 |
| 4,827,048 | 5/1989 | Knifton | 568/698 |
| 5,164,354 | 11/1992 | Aldridge et al. | 502/220 |
| 5,420,092 | 5/1995 | Soled et al. | 502/210 |

FOREIGN PATENT DOCUMENTS

| | | |
|---|---|---|
| 844004 | 6/1970 | Canada . |
| 0123713 | 11/1984 | European Pat. Off. . |
| 0596859 | 5/1994 | European Pat. Off. . |
| 7076540 | 3/1995 | Japan . |
| 7118186 | 5/1995 | Japan . |
| 1281120 | 7/1972 | United Kingdom . |
| 1306141 | 2/1973 | United Kingdom . |
| 1371905 | 10/1974 | United Kingdom . |
| 1476534 | 6/1977 | United Kingdom . |
| 1570650 | 7/1980 | United Kingdom . |
| 9420212 | 9/1994 | WIPO . |
| WO9513869 | 5/1995 | WIPO . |

*Primary Examiner*—Glenn Caldarola
*Assistant Examiner*—Nadine Preisch
*Attorney, Agent, or Firm*—Brooks Haidt Haffner & Delahunty

[57] ABSTRACT

This invention relates to a novel catalyst composition comprising a heteropolyacid and a siliceous support which is in the form of extrudates or pellets and to a process for hydrating olefins to the corresponding alcohols in the vapour phase in the presence of such a catalyst composition. By using the specific catalyst composition described herein it is possible not only to increase the space-time-yield of a process but also to prolong the life thereof thereby reducing the frequency with which the catalyst is changed or replaced on a plant, especially in an olefin hydration process.

8 Claims, No Drawings

5,714,429

SUPPORTED HETEROPOLYACID CATALYST ON A SILICA SUPPORT FORMED BY FLAME HYDROLYSIS

The present invention relates to a novel catalyst composition comprising heteropolyacid catalyst supported on a specific type of silica and to a process for the hydration of olefins using said catalyst composition.

Prior art publications such as eg GB-A-1281120 describe a liquid phase process for the hydration of olefins using a heteropolyacid catalyst. Furthermore, U.S. Pat. No. 2,173,187 describes a process for the hydration of olefins in the vapour phase to the corresponding alcohols by using as catalyst heteropolyacid, the complex anion of which includes one element from group VI, sub-group A of the Periodic table. It is stated in this reference that the catalyst can be used with or without a support. The supports, when used, are said to be preferably silica gel although other siliceous supports such as silcic acid, Japanese acid clay, bentonite, kieselguhr, or asbestos are also listed.

Hydration of olefins such as ethylene or propylene to the corresponding alcohols by hydration thereof in the vapour phase using a phosphoric acid catalyst deposited on a siliceous support is well known. Numerous prior art publications described such a procedure including those disclosed in GB-A-1570650, U.S. Pat. No. 4,808,559, GB-A-1371905, U.S. Pat. No. 4,038,211, U.S. Pat. No. 4,012,452, GB-A-1476534, GB-A-1306141, U.S. Pat. No. 3,996,338 and CAN-A-844004. In each of these prior publications, the nature of the siliceous support used is defined by various parameters including the pore volume, the surface area, the crush strength and the purity of the support. However, none of these documents identify the precise combination of the support and a heteropolyacid catalyst for this purpose.

It has now been found that by carefully controlling the aspects referred to above and especially by using silica supports of a particular physical form, it is possible to design a heteropolyacid catalyst system having improved performance.

Accordingly, the present invention is a catalyst composition comprising a heteropolyacid and a siliceous support characterised in that the siliceous support is in the form of extrudates or pellets.

The siliceous support used is most preferably derived from an amorphous, non-porous synthetic silica especially fumed silica, such as those produced by flame hydrolysis of $SiCl_4$. Specific examples of such siliceous supports include Support 350 made by pelletisation of AEROSIL® 200 (both ex Degussa). This pelletisation procedure is suitably carried out by the process described in U.S. Pat. No. 5,086,03 1 (see especially the Examples) and is incorporated herein by reference. Such a process of pelletisation or extrusion does not involve any steam treatment steps and the porosity of the support is derived from the interstices formed during the pelletisation or extrusion step of the non-porous silica. The silica support is suitably in the form of pellets or beads or are globular in shape having a particle diameter of 2 to 10 mm, preferably 4 to 6 mm. The siliceous support suitably has a pore volume in the range from 0.3–1.2 ml/g, preferably from 0.6–1.0 ml/g. The support suitably has a crush is strength of at least 2 Kg force, suitably at least 5 Kg force, preferably at least 6 Kg and more preferably at least 7 Kg. The crush strengths quoted are based on average of that determined for each set of 50 beads/globules on a CHATTILLON tester which measures the minimum force necessary to crush a particle between parallel plates. The bulk density of the support is suitably at least 380 g/l, preferably at least 440 g/l.

The support suitably has an average pore radius (prior to use) of 10 to 500 ÅAngstroms, preferably an average pore radius of 30 to 100 ÅAngstroms.

In order to achieve optimum performance, the siliceous support is suitably free of extraneous metals or elements which might adversely affect the catalytic activity of the system. The siliceous support suitably has at least 99% w/w purity, ie the impurities are less than 1% w/w, preferably less than 0.60% w/w and more preferably less than 0.30% w/w.

The term "heteropolyacids" as used herein and throughout the specification is meant to include the free acids and salts thereof. The heteropolyacids used to prepare the olefin hydration catalysts of the present invention therefore include the free acids and the coordination-type salts thereof in which the anion is a complex, high molecular weight entity. Typically, the anion is comprises 2–18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I–VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known eg as Keggin, Wells-Dawson and Anderson-Evans-Perloff structures.

Heteropolyacids usually have a high molecular weight—eg in the range from 700–8500 and include dimeric complexes. They have a relatively high solubility in polar solvents such as water or other oxygenated solvents, especially if they are free acids and in the case of several salts, and their solubility can be controlled by choosing the appropriate counterions. Specific examples of heteropolyacids that may be used as the catalysts in the present invention include:

12-tungstophosphoric acid—$H_3[PW_{12}O_{40}].xH_2O$
12-molybdophosphoric acid—$H_3[PMo_{12}O_{40}].xH_2O$
12-tungstosilicic acid—$H_4[SiW_{12}O_{40}].xH_2O$
12-molybdosilicic acid—$H_4[SiMo_{12}O_{40}].xH_2O$
Potassium tungstophosphate—$K_6[P_2W_{18}O_{62}].xH_2O$
Sodium molybdophosphate—$Na_3[PMo_{12}O_{40}].xH_2O$
Ammonium molybdodiphosphate—$(NH_4)_6[P_2Mo_{18}O_{62}].xH_2O$
Sodium tungstonickelate—$Na_4[NiW_6O_{24}H_6].xH_2O$
Ammonium molybdodicobaltate—$(NH_4)[Co_2Mo_{10}O_{36}].xH_2O$
Cesium hydrogen tungstosilicate—$Cs_3H[SiW_{12}O_{40}].xH_2O$
Potassium molybdodivanado phosphate—$K_5[PMoV_2O_{40}].xH_2O$ The impregnated support is suitably prepared by dissolving the heteropolyacid in eg distilled water, and then adding the support to the aqueous solution so formed. The support is suitably left to soak in the acid solution for a duration of several hours, with periodic manual stirring, after which time it is suitably filtered using a Buchner funnel in order to remove any excess acid.

The wet catalyst thus formed is then suitably placed in an oven at elevated temperature for several hours to dry, after which time it is allowed to cool to ambient temperature in a dessicator. The weight of the catalyst on drying, the weight of the support used and the weight of the acid on support was obtained by deducting the latter from the former from which the catalyst loading in g/liter was determined.

This catalyst (measured by weight) can then be used in the organic reactions such as eg an olefin hydration process.

It should be noted that the polyvalent oxidation states and hydration states of the heteropolyacids as stated previously and as represented in the typical formulae of some specific compounds only apply to the fresh acid before it is impregnated onto the support, and especially before it is subjected to the olefin hydration process conditions. The degree of hydration of the heteropolyacid may affect the acidity of the catalyst and hence its activity. Thus, either or both of these actions of impregnation and olefin hydration process may possibly change the hydration and oxidation state of the metals in the heteropolyacids, ie the actual catalytic species under the process conditions may not retain the hydration/ oxidation states of the metals in the heteropolyacids used to is impregnate the support. Naturally, therefore, it is to be expected that such hydration and oxidation states may also be different in the spent catalysts after the reaction.

According to a further embodiment, the present invention is a process for hydrating olefins to the corresponding alcohols in the vapour phase in the presence of a catalyst composition comprising a heteropolyacid catalyst supported on a siliceous support characterised in that the siliceous support is in the form of extrudates or pellets as hereinabove defined.

The process is suitably carried out using the following reaction conditions:

a. the mole ratio of water to olefin passing through the reactor is suitably in the range from 0.1–3.0, preferably 0.1–1.0 b. the gas hourly space velocity (GHSV) of the water/ olefin mixture is suitably from 0.010 to 0.25 g/min/cm$^3$ of the catalyst system, preferably from 0.03–0.10 g/min/cm$^3$ of the catalyst composition.

c. the heteropolyacid catalyst concentration is from 5 to 60% w/w based on the total weight of the catalyst system, preferably from 10–30% w/w of the total weight of the catalyst composition.

The supported heteropolyacid catalysts may also be further modified by the addition of phosphoric acid or other mineral acids thereto.

The olefin hydration reaction is carried out at a temperature from 150°–350° C. Within this temperature range, the hydration of ethylene to ethanol is suitably carried out at a temperature in the range from dew point of the feed gases to 350° C., and preferably from 200°–300° C.; the hydration of propylene to isopropanol is suitably carried out at a temperature in the range from its dew point to 300° C., and is preferably from 150°–250° C.

The hydration reaction is carried out at a pressure ranging from 1000–25000 KPa.

The olefins to be hydrated are suitably ethylene or propylene and the corresponding alcohols formed are suitably ethanol, n-propanol and isopropanol respectively. These olefins may be used pure or as a mixture of olefins to generate a corresponding mixture of alcohols. Thus mixed hydrocarbon feedstocks emerging from eg a refinery such as from a fluid catalytic cracking process and comprising a mixture of C2 and C3 saturated and unsaturated hydrocarbons can be used for this purpose. The process is carried out in the vapour phase, ie both the olefin and water are in the vapour phase over the catalyst system, apart from a small proportion of each gaseous reactant which dissolves in the catalyst system. The hydration reaction is believed to occur between such dissolved reactants. Ethers corresponding to the olefin are formed as by-products during the reaction.

The hydration reaction is carried out by placing the catalyst composition in a reactor, sealing the reactor and then heating the catalyst composition to the reaction temperature. The catalyst composition is heated to a temperature from 170° to 300° C. depending upon the end product desired. For instance, if the end product is ethanol from ethylene, the catalyst composition is suitably heated from 225° to 280° C., preferably from 230°–260° C., more preferably from 235°–245° C. On the other hand, if the end product is n-propanol or iso-propanol from propylene, the catalyst composition is suitably heated from 180°–225° C., preferably from 185°–205° C. When the catalyst composition has attained the desired temperature a charge of the olefin and water in the vapour state is passed through the reactor. The mole ratio of water to olefin passing through the reactor is suitably in the range from 0.1 to 3.0, preferably from 0.1 to 1.0, more preferably from 0.25–0.45. The space velocity of water vapour/olefin mixture passing through the reactor is subject to slight variations depending upon whether the reactant olefin is ethylene or propylene. For instance, in the case of ethylene, the space velocity of the mixture thereof with water vapour is suitably from 0.010 to 0.100, preferably from 0.020 to 0.050 grammes per minute per cm$^3$ of the catalyst composition. In the case of a mixture of propylene and water vapour, the space velocity is suitably in the from 0.010–0.100, preferably from 0.02–0.07 g/min/cm$^3$ of the catalyst composition.

The hydration reaction is carried out a pressure ranging from 1000 to 25000 KPa. Within this range the hydration of ethylene is suitably carried out at a pressure from 3000 to 10000 KPa, whereas the hydration of propylene is suitably carried out at a pressure from 2000–7600 KPa.

The activity of the catalyst composition was measured by monitoring the total amount of alcohol, ether and unreacted olefin produced over a ten-hour period at standard test conditions (specified in the Examples below), once a steady state had been reached in the pilot plant.

Alcohol and ether production was measured by gas chromatography using a Perkin Elmer Auto system GC (see below), whereas unreacted olefin was metered using a wet-type positive displacement flow meter (ex Alex Wright & Co, Model DM3A).

A very important and unexpected feature of the present invention which distinguishes it over the conventional catalyst compositions for hydration of olefins is that the siliceous support used retains its initial crush strength even after prolonged use is which extends to the total life of the catalyst composition. In fact, in some instances, the crush strength of the support has been shown to increase after use rather than decrease as would be expected with all conventional supports of the silica gel type used hitherto. This is the case even when the initial crush strength of the conventional supports is the same as or greater than the supports now used. In the current set of olefin hydration tests carried out with the catalyst compositions now claimed, a significant rise in the crush strength was noted after the catalyst composition has been subjected to the olefin hydration process conditions. In the Examples shown in Table 8 below, the catalyst system had been on stream for ca. 550 hours. In contrast, most conventional silica gel based systems would begin to lose their crush strength after having been on stream for this length of time, thereby reducing the life of the support used and hence the catalyst composition has to be replaced frequently.

Thus, it has now been found that by using the specific support described herein it is possible not only to increase the space-time-yield (hereafter "STY") of the process but also to prolong the life of the support thereby reducing the frequency with which the support is changed or replaced on a plant.

The present invention is further illustrated with reference to the following

EXAMPLES 1–8

Description of the General Procedure & Equipment Used

All the examples to measure the performance of the heteropolyacids/silica catalysts for isopropanol production were carried out under continuous flow conditions using a small copper lined tubular reactor containing 50 ml of the catalyst composition. Water and propylene (>99% v/v) were fed to this reactor by metering pumps, and passed through a pre-heater/vapouriser prior to entering the zone containing the catalyst composition.

The reactor was isothermally heated using a fluidized bath, the temperature of which was controlled to within ±0.5° C. The pressure of the process was measured at the inlet of the reactor, and was controlled to within ±1 psig.

The gaseous product stream exiting the reactor was then dropped in pressure to approximately ambient, condensed and degassed. The off-gas was then thoroughly scrubbed with water to remove any residual alcohol, and the gas (mainly consisting of unreacted propylene) was then accurately metered prior to being vented.

The activity of each of the catalyst compositions tested was assessed by collecting the condensed product, plus all the scrubbing water, over a 10 hour test period, and then by analysing each stream for isopropanol, n-propanol and acetone content. The total production of each compound is simply the sum of amount of compound found in the condensate and the scrubbing water.

The above procedure was used to test four catalyst compositions in order to establish the superiority of the heteropolyacid/silica catalyst composition of the present invention (compositions (c) and (d) below) over the conventional commercial phosphoric acid/montmorillonite based systems (systems (a) and (b) below, not according to the invention). The catalyst compositions tested were:

a. a commercial phosphoric acid (160 g) on a fresh montmorillonite based support (1 liter) (ex Chemische Werke Hüls).

b. as in (a) above but which has been re-soaked in fresh ortho-phosphoric acid to give an acid loading of 180 g/l.

c. 12-tungstophosphoric acid supported on pelletised fumed silica (Support 350, ex Degussa), to give an acid loading of 104 g/l.

d. 12-tungstosilicic acid supported on pelletised fumed silica (Support 350, ex Degussa), to give an acid loading was 108 g/l.

The catalyst compositions of the present invention described in (c) and (d) above were prepared as follows:

Catalyst Composition (c): 104 g/l 12-Tungstophosphoric Acid on Support 350

61.6724 g of 12 tungstophosphoric acid (ex Fisons Ltd, AR Grade) was dissolved in 250 ml of distilled water, and added to 97.03 g (200 ml) of Support 350 (ex Degussa, bulk density of batch=486 g/l). The support was left to soak in the acid solution for 26 hours, with periodic manual stirring, after which time it was filtered using a Buchner funnel in order to remove any excess acid.

The wet catalyst thus formed was then placed in an oven at 120° C. for 24 hours to dry, after which time it was allowed to cool to ambient temperature in a dessicator. The weight of the catalyst on drying was 117.84 g, the weight of the support used was 97.03 g (=200 ml, to the nearest pellet) and the weight of the acid on support was obtained by deducting the latter from the former (ie 117.84−97.03=20.81 g in 200 ml) which corresponds to 104 g/l.

50.0 ml of this catalyst composition (measured by weight) was then used in the experiments described below.

Catalyst Composition (d): 108 g/l 12-Tunstosilicic Acid on Support 350

73.0301 g of 12-Tungstosilicic acid (ex Fisons Ltd) was dissolved in 250 ml of distilled water, and added to 97.03 g (200 ml) of Support 350 (ex Degussa, bulk density of batch=486 g/l). The support was left to soak in the acid solution for 40 hours, with periodic manual stirring, after which time it was filtered using a Buchner funnel in order to remove any excess acid.

The wet catalyst thus formed was then placed in an oven at 120° C. for 45 hours to dry, after which time it was allowed to cool to ambient temperature in a dessicator. The weight of the catalyst on drying was 118.59 g, the weight of the support used was 97.03 g (=200 ml, to the nearest pellet) and the weight of the acid on support was obtained by deducting the latter from the former (ie 118.59−97.03=21.56 g in 200 ml) which corresponds to 108 g/l.

50.0 ml of this catalyst composition (measured by weight) was then used in the experiments described below.

The results of the experiments carried out are summarised in Tables 1–8 below:

The supports in the catalyst systems used in the Examples had the following physical characteristics:

| CHARACTERISTICS | SUPPORT 350 (ex DEGUSSA) |
| --- | --- |
| Pore vol ml/g | 0.82 |
| ml/l cat vol | 400 |
| Bulk Density g/l | 488 |
| Crush strength (Kg) | |
| Fresh support | 7 |
| Fresh Cat Composition (c) | 9.2 |
| Used Cat Composition (c) | 11.5 |
| Attrition % w/w | |
| Fresh support | <1.3 |
| Fresh Catalyst Composition | N/D |
| Mean Pore Radius Fresh Support (Å) | 77 |

EXAMPLE 1

The results in Table 1 below compare production of isopropanol using conventional commercial phosphoric acid/montmorillonite based catalyst systems when used fresh (a) and when used after resoaking in orthophosphoric acid (b) with the heteropolyacid/silica catalyst composition (d) of the present invention. In this case, the reaction pressures used were 565 psig (3895.7 KPa), the water to propylene mole ratio was 0.32, the GHSV of propylene/ water mixture was 0.054/g/min/cc of catalyst. N/D in the Table 1 means not determined.

TABLE 1

| Reaction Temp. (°C.) | Fresh Commercial Cat System (a) STY (G/L/H) | Resoaked Commercial Cat System (b) STY (G/L/H) | Cat Compn (d) of Invention STY (G/L/H) |
| --- | --- | --- | --- |
| 200 | 179.5 | 190.9 | N/D |
| 195 | 168 | N/D | 184.4 |
| 190 | 176.3 | 195.4 | 214.9 |
| 187 | N/D | N/D | 238.4 |
| 185 | N/D | 191.5 | 249.8 |
| 183 | IMPOSSIBLE | IMPOSSIBLE | 258.4 |
| 182 | TO | TO | 271.1 |
| 181 | OPERATE | OPERATE | 278.1 |
| 180 | IN | IN | 281.2 |
| 179 | THIS | THIS | 283.6 |
| 178 | REGION | REGION | 289.1 |
| 177 | DUE | DUE | 291.0 |
| 176 | TO | TO | 296.2 |
| 175 | ACID | ACID | 299.8 |
| 174 | WEEPING | WEEPING | 302.1 |
| 173 | FROM | FROM | 301.3 |
| 172 | SUPPORT | SUPPORT | 246.8 |

EXAMPLE 2

The results in Table 2 below compare the space-time yield of isopropanol (ie grams/liter of catalyst/hour) from propylene at varying water to propylene mole ratios. In the process according to the invention using catalyst composition (d), the mole ratios of water to propylene were 0.43 and 0.32 respectively. In each case, the reaction pressure was 565 psig (3895.7 KPa) and the GHSV of propylene was 0.047 g/min/cc catalyst composition (the GHSV of water being variable in order for the mole ratio to change).

TABLE 2

| Reaction Temp (°C.) | STY of Isopropanol at Propylene/water Mole Ratio of 0.43 | STY of Isopropanol at Propylene/water Mole Ratio of 0.32 |
| --- | --- | --- |
| 195 | 256.7 | 184.4 |
| 190 | 298.5 | 214.9 |
| 187 | 314 | 238.0 |
| 185 | 310.3 | 249.8 |
| 183 | 307.5 | 258.4 |

EXAMPLE 3

A further set of experiments was conducted at varying temperatures and pressures to determine the effect of pressure on the STY of isopropanol using the catalyst composition (d). In this set, the water to propylene mole ratio used was 0.32 and the GHSV of the propylene/water mixture was 0.054 g/min/cc of catalyst composition. The results are tabulated below in Table 3 (N/D=not determined).

TABLE 3

| Reaction Temp (°C.) | Isopropanol STY at 3206.2 KPa | Isopropanol STY at 3895.7 KPa | Isopropanol STY at 4585.2 KPa |
| --- | --- | --- | --- |
| 190 | N/D | 214.9 | 259.4 |
| 187 | N/D | 238.0 | 282.3 |
| 185 | N/D | 249.8 | 292.8 |
| 184 | N/D | N/D | 292.0 |
| 183 | N/D | 258.4 | 292.7 |
| 181 | N/D | 278.1 | 302.5 |
| 180 | 242.1 | 281.2 | 287.1 |
| 175 | 266.2 | 299.8 | BELOW |
| 173 | N/D | 301.3 | DEW |
| 172 | 275.1 | 246.8 | POINT |
| 170 | 268.4 | BELOW | |
| 168 | 267.8 | DEW | |
| 167 | 258.0 | POINT | |
| 166 | 266.1 | | |

EXAMPLE 4

The procedure used for Example 1 above was repeated to compare the rate of production of isopropanol from propylene using catalyst composition (c) according to the invention with a fresh and a resoaked phosphoric acid/ montmorillonite based catalyst system (both commercial). The fresh catalyst had a catalyst loading of 160 g/liter (ex H üls) whereas in the resoaked catalyst the loading was maintained at about 180 g/liter. These experiments were conducted at a reaction pressure of 565 psig (3895.7 KPa) and a water to propylene mole ratio in the feed gas of 0.32. The GHSV of the propylene/water mixture was 0.054 g/min/cc. The results are shown in Table 4 below (N/D=not determined):

TABLE 4

| Reaction Temp. (°C.) | Fresh Commercial Catalyst System STY (G/L/H) | Resoaked Commercial Catalyst System STY (G/L/H) | Cat Compn (d) of Invention STY (G/L/H) |
| --- | --- | --- | --- |
| 200 | 179.5 | 190.9 | 204.1 |
| 195 | 168 | N/D | 224.7 |
| 190 | 176.3 | 195.4 | 235.1 |

EXAMPLE 5

The process of Example 3 at various reaction pressures was repeated but now using catalyst composition (c) according to the invention which had 104 g/l of 12-tungstophosphoric acid on synthetic silica Support 350 (ex Degussa). The GHSV of propylene/water mixture was 0.054 g/min/cc of catalyst and the water to propylene mole ratio in the feed gas was 0.32. The results are tabulated in Table 5 below:

TABLE 5

| Reaction Temp. (°C.) | Isopropanol STY at 3206.2 KPa | Isopropanol STY at 3895.7 KPa | Isopropanol STY at 4585.2 KPa |
| --- | --- | --- | --- |
| 200 | 177.05 | 204.1 | 229.8 |
| 195 | 190.2 | 224.7 | 240.7 |
| 190 | 205.8 | 235.1 | N/D |
| 185 | 207.7 | N/D | N/D |

N/D = not determined

EXAMPLE 6

A set of experiments were carried out using the catalyst composition (c) of the present invention to determine the effect of the duration of the reaction ie time on stream, on the STY (g/l/hour) of isopropanol and normal propanol in the process. The GHSV for the propylene water mixture in this case was 0.054 g/min/cc of catalyst composition, the reaction temperature used was 190° C. and the reaction pressure was 565 psig (3895.7 KPa). The results are tabulated below in Table 6.

TABLE 6

| Days on Stream | Isopropanol STY | n-Propanol STY |
| --- | --- | --- |
| 6.1 | 235.1 | 0.593 |
| 17.9 | 231.2 | 0.516 |
| 19 | 231.5 | 0.521 |
| 19.7 | 232.4 | 0.525 |
| 22.2 | 232.9 | 0.523 |

EXAMPLE 7

The process of Example 6 was repeated but now using the catalyst composition (d) according to the invention and a reaction temperature of 180° C. The results are tabulated below in Table 7.

TABLE 7

| Days on Stream | Isopropanol STY | n-Propanol STY |
| --- | --- | --- |
| 9 | 281.2 | 1.28 |
| 14 | 280.2 | 1.12 |
| 26 | 279.73 | 0.96 |

EXAMPLE 8

Finally, a set of experiments were carried out to determine the variation in crush strength of the unused and used catalyst compositions both in the case of the composition (c) of the present invention and those of the commercial catalyst system (a). The duration of use was 23 days on stream after which the crush strength of the "used" catalyst compositions were determined. The results are tabulated below:

TABLE 8

| Catalyst System | Crush Strength (Fresh) | Crush Strength (Used) |
| --- | --- | --- |
| (a) | 4 Kg | 7 Kg |
| (c) | 9.2 Kg | 11.2 Kg |

EXAMPLES 9–12

Ethanol Production

Description of the General Procedure and Equipment Used

All experiments to measure the performance of heteropolyacid/silica catalyst compositions for ethanol production were carried out in the vapour phase under continuous flow conditions using a small copper lined tubular reactor containing 50 ml of hydration catalyst composition. Distilled water was fed to the reactor via a metering pump whereas ethylene (>99% vol/vol) was fed to the reactor via a compressor. The flow of ethylene was measured using an orifice plate & D.P. cell, and was controlled using a computer controlled flow control valve. Both streams were combined, and were then passed through a preheater/vapouriser prior to entering the catalyst composition zone.

The reactor was isothermally heated using a fluidsed bath, the temperature of which was controlled to within ±0.5° C. The pressure of the process was measured at the inlet of the reactor, and was controlled to within ±1 psig.

The gaseous product stream exiting the reactor was then dropped in pressure to approximately ambient, condensed, & degassed. The off-gas was then thoroughly scrubbed with water to remove any residual alcohol, and the gas (mainly unreacted ethylene, plus traces of diethylether) was then accurately metered prior to being vented.

The activity of a catalyst composition was assessed by collecting the condensed product, plus all the scrubbing water, over a 10 hour test period, and then analysing each stream for ethanol, acetaldehyde, & s-butanol content. The total production of each compound is simply the sum of amount of compound found in the condensate & the scrubbing water.

Catalysts Tested

Three catalysts compositions were tested on the above equipment to demonstrate the superiority of HPA/silica catalyst composition over the conventional H3PO4/silica commercial catalyst systems.

e) A catalyst composition in which phosphoric acid is supported on pelletised fumed silica (Support 350, ex. Degussa) to an acid loading of 293 g/l.

f) A catalyst composition in which 12-tungstosilicic acid (TSA) is supported on pelletised fumed silica (Degussa 350), to give an acid loading of 108 g/l. This catalyst composition was prepared in an identical way to catalyst (d), which is described above.

g) A catalyst composition in which 12-tungstophosphoric acid (TPA) is supported on pelletised fumed silica (Degussa 350), to give an acid loading of 173 g/l. This catalyst composition was prepared in an identical way to catalyst composition (c), which is described above, except that the concentration of acid used to impregnate the support has higher (430.3 g/l).

In all cases, 50.0 ml of catalyst composition (measured by weight) was then placed in the autoclave described above and tested for ethylene hydration activity.

EXAMPLE 9

The results in Table 9 below compare production of ethanol using conventional commercial orthophosphoric/fumed silica catalyst compositions with the heteropolyacid/fumed silica catalyst compositions (f) & (g). In this case, the reaction pressure used was 1000 psig (6895 KPa), the water:ethylene mole ratio was 0.30, and the GHSV of the ethylene/water mixture was 0.029 g/min/cm$^3$ of catalyst composition.

TABLE 9

| | ETHANOL PRODUCTION (G/LITER CAT/HR) USING | | |
| --- | --- | --- | --- |
| Reaction Temp (°C.) | Commercial H$_3$PO$_4$/silica Catalyst (e)* | Catalyst Compn (f) TSA/SiO$_2$ (108 g/l) | Catalyst Compn (g) TPA/SiO$_2$ (173 g/l) |
| 235 | 54.7 | 97.1 | 77.8 |
| 240 | 71.5 | 102.9 | 86.2 |
| 245 | 80.8 | 97.3 | 90.7 |
| 250 | 85.3 | 93.8 | ND |
| 255 | 90.7 | 89.9 | ND |

*-comparative test not according to the invention
ND-not determined

EXAMPLE 10

The results in Table 10 below compare production of s-butanol using conventional commercial orthophosphoric/fumed silica catalyst systems, with the heteropolyacid/fumed silica catalyst compositions (f) & (g). In this case, the reaction pressure used was 1000 psig (6895 KPa), the water:ethylene mole ratio was 0.30, and the GHSV of the ethylene/water mixture was 0.029 g/min/cm$^3$ of catalyst composition.

TABLE 10

| | s-BUTANOL PRODUCTION (G/LITER CAT/HR) USING | | |
|---|---|---|---|
| Reaction Temp (°C.) | Commercial $H_3PO_4$/silica Catalyst (a)* | Catalyst Compn (f) TSA/SiO$_2$ (108 g/l) | Catalyst Compn (g) TPA/SiO$_2$ (173 g/l) |
| 235 | 0.006 | 0.08 | 0.09 |
| 240 | 0.016 | 0.16 | 0.10 |
| 245 | 0.019 | 0.173 | 0.08 |
| 250 | 0.027 | 0.12 | ND |
| 255 | 0.027 | 0.08 | ND |

*-comparative test not according to the invention
ND-not determined

EXAMPLE 11

The results in Table 11 below compare production of ethanol using the heteropolyacid/fumed silica catalyst composition (f), at a variety of different reaction pressures. In this case, the reaction pressures used were 700 psig (4827 KPa), 800 psig (5516 KPa), & 900 psig (6206 KPa); the water:ethylene mole ratio was 0.30; and the GHSV of the ethylene/water mixture was 0.029 g min/cm$^3$ of catalyst composition.

TABLE 11

| | ETHANOL PRODUCTION (G/LITER CAT/HR) USING | | |
|---|---|---|---|
| Reaction Temp (°C.) | Reaction Pressure (700 psig) | Reaction Pressure (800 psig) | Reaction Pressure (900 psig) |
| 220 | 54.5 | ND | ND |
| 225 | 72.4 | 73.6 | 69.6 |

ND-not determined

EXAMPLE 12

In all of the above experiments, care was taken to measure the pH of the reaction product in order to assess the acid loss rate from the catalyst. Loss of acid is a particular problem for phosphoric acid/silica systems, and, over time, leads to significant catalyst deactivation. The pH of the reaction product from a phosphoric acid/silica catalyst is typically between 3 & 5, depending on process conditions. However the pH of the reaction products from the heteropoly acid/silica catalyst compositions used in the above examples was typically 6–7. This indicates minimal acid loss is taking place. The only exception to this is a short period (ca. 5–10 hrs) on start-up when the pH tends to be slightly acidic (ca. pH 4–5). It is believed that this is due to the production of traces of carboxylic acids on start-up, rather than acid being lost from the catalyst composition.

The results clearly show that HPA catalysts supported on Degussa 350 are significantly more active for ethanol production than H3PO4/silica based systems.

I claim:

1. A catalyst composition comprising a heteropolyacid catalyst supported on an amorphous, non-porous, synthetic silica produced by flame hydrolysis of SiCl$_4$ and in the form of an extrudate or pellet.

2. A catalyst composition comprising a heteropolyacid catalyst supported on an amorphous, non-porous synthetic fumed silica and in the form of an extrudate or pellet.

3. A catalyst composition according to claim 1 or 2 wherein the siliceous support is in the form of pellets or beads or are globular in shape having a particle diameter of 2 to 10 mm, has a pore volume in the range from 0.3–1.2 ml/g and crush strength of at least 2 Kg force.

4. A catalyst composition according to claim 1 or 2 wherein the siliceous support is free of extraneous metals or elements capable of adversely affecting the catalytic activity of the system and has at least 99% w/w purity.

5. A catalyst composition according to claim 1 or 2 wherein the heteropolyacids include the free acids and the coordination salts thereof in which the anion is a complex, high molecular weight entity and comprises 2–18 oxygen-linked polyvalent metal peripheral atoms surrounding a central atom or ion from Groups I–VIII in the Periodic Table of elements.

6. A catalyst composition according to claim 5 wherein the polyvalent metal peripheral atom is one or more of molybdenum, tungsten, vanadium, niobium and tantalum and the central atom or ion is selected from silicon; phosphorus; cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; and hexavalent tellurium ions; and heptavalent iodine ions.

7. A catalyst composition according to claim 1 or 2 wherein the heteropolyacid comprises at least one of the following compounds:

1-12-tungstophosphoric acid—$H_3[PW_{12}O_{40}].xH_2O$ 1-12-molybdophosphoric acid—$H_3[PMo_{12}O_{40}].xH_2O$ 1-12-tungstosilicic acid—$H_4[SiW_{12}O_{40}].xH_2O$ 1-12-molybdosilicic acid—$H_4[SiMo_{12}O_{40}].xH_2O$ Potassium tungstophosphate—$K_6[P_2W_{18}O_{62}].xH_2O$ Sodium molybdophosphate—$Na_3[PMo_{12}O_{40}].xH_2O$ Ammonium molybdodiphosphate—$(NH_4)_6[P_2Mo_{18}O_{62}].xH_2O$ Sodium tungstonickelate—$Na_4[NiW_6O_{24}H_6].xH_2O$ Ammonium molybdodicobaltate—$(NH_4)[Co_2Mo_{10}O_{36}].xH_2O$ Cesium hydrogen tungstosilicate—$Cs_3H[SiW_{12}O_{40}].xH_2O$ Potassium molybdodivanado phosphate—$K_5[PMoV_2O_{40}].xH_2O$.

8. A catalyst composition according to claim 1 or 2 wherein the supported heteropolyacid catalyst composition is further modified by the addition of a mineral acid optionally comprising phosphoric acid.

* * * * *

UNITED STATES PATENT AND TRADEMARK OFFICE
CERTIFICATE OF CORRECTION

PATENT NO. : 5,714,429
DATED : February 3, 1998
INVENTOR(S) : GORDON J. HAINING

It is certified that error appears in the above-identified patent and that said Letters Patent is hereby corrected as shown below:

Column 2, lines 2 and 3, delete "Å"

Column 5, line 44, change "heteropotyacid/silica" to --heteropolyacid/silica--.

Signed and Sealed this

Twenty-third Day of June, 1998

Attest:

BRUCE LEHMAN

*Attesting Officer*  *Commissioner of Patents and Trademarks*